US012807930B2

(12) United States Patent
Clarke et al.

(10) Patent No.: US 12,807,930 B2
(45) Date of Patent: Nov. 24, 2026

(54) METHOD OF PURIFYING A COMPOSITION COMPRISING A GROUP B ADENOVIRUS

(71) Applicant: AKAMIS BIO, INC., Cambridge, MA (US)

(72) Inventors: Peter Clarke, Cambridge, MA (US); Simon Alvis, Abingdon (GB)

(73) Assignee: Akamis Bio, Inc., Cambridge, MA (US)

( * ) Notice: Subject to any disclaimer, the term of this patent is extended or adjusted under 35 U.S.C. 154(b) by 1115 days.

(21) Appl. No.: 17/596,717

(22) PCT Filed: Jun. 24, 2020

(86) PCT No.: PCT/EP2020/067668
§ 371 (c)(1),
(2) Date: Dec. 16, 2021

(87) PCT Pub. No.: WO2020/260374
PCT Pub. Date: Dec. 30, 2020

(65) Prior Publication Data

US 2022/0340885 A1 Oct. 27, 2022

(30) Foreign Application Priority Data

Jun. 25, 2019 (GB) ...................................... 1909081

(51) Int. Cl.
*C12N 7/02* (2006.01)

(52) U.S. Cl.
CPC ...... *C12N 7/02* (2013.01); *C12N 2710/10051* (2013.01); *C12N 2710/10351* (2013.01)

(58) Field of Classification Search
CPC ............ C12N 7/02; C12N 2710/10051; C12N 2710/10351; C12N 2710/10332; C12N 7/00; A61K 35/761; C07K 14/075
(Continued)

(56) References Cited

U.S. PATENT DOCUMENTS 5,595,756 A 1/1997 Bally et al.
7,235,391 B2 6/2007 Wu et al.
(Continued)

FOREIGN PATENT DOCUMENTS

AU 2010244348 A1 12/2011
CA 2244213 A1 8/1997
(Continued)

OTHER PUBLICATIONS

International Search Report and Written Opinion of PCT/EP2020/067668, dated Nov. 5, 2020.
(Continued)

*Primary Examiner* — Madeline Gonzalez
(74) *Attorney, Agent, or Firm* — COOLEY LLP; Andrew T. Wilkins; David M. Lee

(57) ABSTRACT

A method of purifying a composition comprising a group B adenovirus, for example comprising a purification step of: subjecting a composition comprising said group B adenovirus to diafiltration employing a diafiltration-buffer with a conductivity of at least 180 $mScm^{-1}$, for example a conductivity of 190, 200, 210, 220, 230, 240, 250, 260, 270, 280, or 290 $mScm^{-1}$. Also provided is a composition obtained using the purification method disclosed herein.

23 Claims, 6 Drawing Sheets

(58) Field of Classification Search
USPC .................................. 210/650, 651, 656, 660
See application file for complete search history.

(56) References Cited

U.S. PATENT DOCUMENTS

| | | | |
|---|---|---|---|
| 7,264,958 B1 | 9/2007 | Transgene | |
| 7,288,251 B2 | 10/2007 | Bedian et al. | |
| 7,351,415 B2 | 4/2008 | Evans et al. | |
| 7,550,296 B2 | 6/2009 | Hermiston et al. | |
| 7,858,367 B2 | 12/2010 | Amalfitano et al. | |
| 8,216,819 B2 | 7/2012 | Hermiston et al. | |
| 9,364,542 B2 | 6/2016 | Chang | |
| 10,034,905 B2 | 7/2018 | Seymour et al. | |
| 11,840,702 B2 | 12/2023 | Champion et al. | |
| 2002/0019051 A1 | 2/2002 | Lusky et al. | |
| 2002/0061592 A1 | 5/2002 | Blanche et al. | |
| 2003/0017138 A1 | 1/2003 | Havenga et al. | |
| 2003/0096787 A1 | 5/2003 | Perricaudet et al. | |
| 2004/0136958 A1 | 7/2004 | Wadell et al. | |
| 2004/0151696 A1 | 8/2004 | Johnson et al. | |
| 2004/0213764 A1 | 10/2004 | Wold et al. | |
| 2005/0153420 A1 | 7/2005 | Konz, Jr. et al. | |
| 2005/0175589 A1 | 8/2005 | Iggo et al. | |
| 2005/0186178 A1 | 8/2005 | Ennist | |
| 2005/0186225 A1 | 8/2005 | Evans et al. | |
| 2006/0140909 A1 | 6/2006 | Wickham et al. | |
| 2006/0292682 A1 | 12/2006 | Hawkins et al. | |
| 2007/0207461 A1 | 9/2007 | Weggeman et al. | |
| 2008/0069836 A1 | 3/2008 | Nabel et al. | |
| 2008/0292592 A1 | 11/2008 | Chada et al. | |
| 2009/0017523 A1* | 1/2009 | Weggeman .............. | C12N 7/00 435/239 |
| 2009/0311219 A1 | 12/2009 | Bonastre et al. | |
| 2010/0047208 A1 | 2/2010 | Ke | |
| 2010/0297072 A1 | 11/2010 | Depinho | |
| 2011/0034560 A1 | 2/2011 | Jacobson et al. | |
| 2012/0283318 A1 | 11/2012 | Mei et al. | |
| 2013/0243731 A1 | 9/2013 | Dias et al. | |

FOREIGN PATENT DOCUMENTS

| | | | |
|---|---|---|---|
| CN | 1241632 | A | 1/2000 |
| CN | 1242051 | A | 1/2000 |
| CN | 1347450 | A | 5/2002 |
| CN | 101381742 | A | 3/2009 |
| CN | 1961961 | A | 5/2010 |
| CN | 102548584 | A | 7/2012 |
| CN | 104640566 | A | 5/2015 |
| EP | 170269 | A2 | 5/2007 |
| JP | 2000504334 | A | 4/2000 |
| JP | 2002541792 | A | 12/2002 |
| JP | 2008531700 | A | 8/2008 |
| JP | 2015526450 | A | 8/2015 |
| WO | WO-1996022378 | A1 | 7/1996 |
| WO | WO-1997021826 | A2 | 6/1997 |
| WO | WO-9822609 | A1 | 5/1998 |
| WO | 1999/018799 | A1 | 4/1999 |
| WO | 00/32754 | A1 | 6/2000 |
| WO | 2000061726 | A1 | 10/2000 |
| WO | 01/11034 | A2 | 2/2001 |
| WO | WO-2005010149 | A2 | 2/2005 |
| WO | WO-2005086922 | A2 | 9/2005 |
| WO | WO-2005107474 | A2 | 11/2005 |
| WO | 2005/118825 | A2 | 12/2005 |
| WO | WO-2006008513 | A1 | 1/2006 |
| WO | WO-2006060314 | A2 | 6/2006 |
| WO | WO-2008080003 | A2 | 7/2008 |
| WO | 2006093924 | A1 | 9/2008 |
| WO | WO-2012024351 | A2 | 2/2012 |
| WO | 2013/026833 | A1 | 2/2013 |
| WO | 2013164754 | A2 | 11/2013 |
| WO | 2014029702 | A1 | 2/2014 |
| WO | WO-2014198852 | A2 | 12/2014 |
| WO | 2015040234 | A1 | 3/2015 |
| WO | 2015/059303 | A1 | 4/2015 |
| WO | WO-2015097220 | A1 | 7/2015 |
| WO | 2015153912 | A1 | 10/2015 |
| WO | WO-2015155370 | A1 | 10/2015 |
| WO | 2015200645 | A1 | 12/2015 |
| WO | WO-2015155370 | A4 | 12/2015 |
| WO | WO-2016030489 | A2 | 3/2016 |
| WO | WO-2016030489 | A3 | 4/2016 |
| WO | WO-2016139463 | A1 | 9/2016 |
| WO | 2016/174200 | A1 | 11/2016 |
| WO | WO-2017103290 | A1 | 6/2017 |
| WO | WO-2017103291 | A1 | 6/2017 |
| WO | WO-2018041827 | A1 | 3/2018 |
| WO | WO-2018041838 | A1 | 3/2018 |
| WO | WO-2018083257 | A1 | 5/2018 |
| WO | WO-2018083258 | A1 | 5/2018 |
| WO | WO-2018083259 | A1 | 5/2018 |
| WO | WO-2018220207 | A1 | 12/2018 |
| WO | WO-2019149829 | A1 | 8/2019 |
| WO | WO-2020260374 | A1 | 12/2020 |

OTHER PUBLICATIONS

Detergents: Triton X-100, Tween-20, and More, Jun. 10, 2020, Mater Methods 2013;3:163.

Clement, N., et al., Construction and production of oncotropic vectors, derived from MVM(p), that share reduced sequence homology with helper plasmids, Cancer Gene Ther. Sep. 2002;9(9):762-70.

Shashkova, E., et al., Characterization of human adenovirus serotypes 5, 6, 11, and 35 as anticancer agents, Virology Nov. 25, 2009;394(2):311-20.

Ferguson, M., et al., Systemic delivery of oncolytic viruses: hopes and hurdles, Advances in Virology, V 2012, Article ID 805629.

Carlisle, R.C., et al., Human erythrocytes bind and inactivate type 5 adenovirus by presenting Coxsackie virus-adenovirus receptor and complement receptor 1, Blood Feb. 26, 2009;113(9):1909-18.

Chau, L.A, et al., HuM291(Nuvion), a humanized Fc receptor-nonbinding antibody against CD3, anergizes peripheral blood T cells as partial agonist of the T cell receptor, Transplantation Apr. 15, 2001;71(7):941-50.

Diehl, K-H, et al., A good practice guide to the administration of substances and removal of blood, including routes and volumes J. Appl. Toxicol, 21, 15-23 (2001).

Hemminki et al., AD3-HTERT-E1A, a Fully Serotype 3 Oncolytic Adenovirus, in Patients With Chemotherapy Refractory Cancer, Molecular Therapy (Aug. 7, 2012), 20(9):1810-1830.

Hotte et al., An Optimized Clinincal Regimen for the Oncolyticvirus PV701, Clinical Cancer Research (Feb. 1, 2007), 13(3):977-985.

Nemunaitis et al., Intravenous Infusion of a Replication-Selective Adenovirus (ONYX-015) in Cancer Patients: Safety, Feasibility and Biological Activity, Gene Therapy (2001), 8:746-759.

Small et al., A Phase I Trial of Intravenous CG7870, a Replication-Selective, Protate-Specific Antigen-Targeted Oncolytic Adenovirus, for the Treatment of Hormone-Refractory, Metastatic Prostate Cancer, Molecular Therapy (Jul. 2006), 14(1):107-117.

European Patent Office, Opposition Division, Decision Revocation of the European Patent No. EP 3007711, Feb. 21, 2023, Munich, Germany.

European Patent Office, Opposition Division, Consolidated List of Cited Opposition Documents, European Patent No. EP 3007711, Dec. 1, 2022, Munich, Germany.

Riedmann, Human Vaccines: News, Human Vaccines & Immunotherapeutics (2012), 8(11):1550-1553.

Auerbach et al., Angiogenesis Assays; Problems and Pitfalls, Cancer and Metastasis Reviews (2000), 19:167-172.

Beans, Targeting Metastasis to Halt Cancer's Spread, PNAS (Dec. 11, 2018), 115 (50):12539-12543.

Gravanis et al., TPA as a Therapeutic Target in Stroke, Expert Opin Ther Targets (Feb. 2008), 12(2):1-18.

Gura, Systems for Identifying New Drugs are Often Faulty, Science (Nov. 7, 1997), 278:1041-1042.

Hait, Anticancer Drug Development: the Grand Challenges, Nature Reviews Drug Discovery (Apr. 2010), 9:253-254.

(56) References Cited

OTHER PUBLICATIONS

Jain, Barriers to Drug Delivery in Solid Tumors, Scientific American (Jul. 1994), 58-65.
Sporn et al., Chemoprevention of Cancer, Carcinogenesis (2000), 21(3):525-530.
Chang, C-M, et al., Treatment of hepatocellular carcinoma with adeno-associated virus encoding interleukin-15 superagonist, Hum Gene Ther. May 2010;21(5):611-21.
Cheng, L., et al., Hyper-IL-15 suppresses metastatic and autochthonous liver cancer by promoting tumour-specific CD8+ T cell responses, J Hepatol. Dec. 2014;61(6):1297-303.
Guo, Y., et al., Immunobiology of the IL-15/IL-15Rα complex as an antitumor and antiviral agent, Cytokine Growth Factor Rev. Dec. 2017;38:10-21.
Ni, S., et al., Evaluation of biodistribution and safety of adenovirus vectors containing group B fibers after intravenous injection into baboons, Hum Gene Ther. Jun. 2005;16(6):664-77.
Fisicaro et al., Versatile Co-Expression of Graft-Protective Proteins Using 2A-Linked Cassettes, Xenotransplantation (2011), 18(2):121-130.
Brument et al., "A versatile and scalable two-step ion-exchange chromatography process for the purification of recombinant adeno-associated virus serotypes-2 and-5," Molecular Therapy (Nov. 2002), 6(5):678-686, doi:10.1006/mthe.2002.0719.
Golovanov et al., "A Simple Method for Improving Protein Solubility and Long-Term Stability," Journal of the American Chemical Society, (Jul. 28, 2004), 126(29):8933-8939.
PCT Application No. PCT/EP2020/067668, International Preliminary Report on Patentability mailed Jan. 6, 2022, Applicant Psioxus Therapeutics Limited.; 7 pages.

* cited by examiner

METHOD OF PURIFYING A COMPOSITION COMPRISING A GROUP B ADENOVIRUS

CROSS-REFERENCE TO RELATED APPLICATIONS

The present application is a 35 U.S.C. § 371 national phase application from, and claims priority to, International Application No. PCT/EP2020/067668, filed Jun. 24, 2020, and published under PCT Article 21(2) in English, which designated the U.S., and claims the benefit of priority from United Kingdom Patent Application No. GB1909081.0 filed on Jun. 25, 2019, and each of which prior applications are incorporated by reference herein into this application in their entirety including all tables, figures and claims.

The present disclosure relates to a method of purifying a composition comprising a group B adenovirus, and purified compositions obtainable from said method.

Background

At the present time the pharmaceutical field is on the edge of realising the potential of viruses as therapeutics for human use. To date a virus derived from ONXY-15 (ONYX Pharmaceuticals and acquired by Shanghai Sunway Biotech) is approved for use in head and neck cancer in a limited number of countries. However, there are a number of viruses currently in the clinic, which should result in some of these being registered for use in humans.

One or more therapies are based on the group B adenovirus EnAd (previously known as ColoAd1) a chimeric oncolytic adenovirus derived from Ad11 (WO 2005/118825 and an armed version of which is disclosed in WO2015/059303 & WO2016/174200 each of which are incorporated herein by reference). EnAd is currently in clinical trials for the treatment of colorectal cancer. As part of the manufacturing process, the virus is propagated in mammalian cells in vitro, for example in a cell suspension culture. The virus is recovered from these cells by cell lysis and subsequent purification. These adenoviral based therapeutic agents need to be manufactured at levels of purity that are free from host cell proteins and under conditions that adhere to good manufacturing practice (GMP).

WO00/32754 discloses a process for preparing highly purified adenoviruses. The disclosure in FIG. 23 and on page 164 of the PCT application can be summarised as follows:

An Ad5 (a group C adenovirus) was released from HEK293 cells by a lysis buffer;

The crude cell lysate containing the Ad5 was clarified by filtration through two 5 micron filters;

The supernatant was then concentrated approximately 10-fold by diafiltration employing the buffer 0.5M Tris, 1 mM $MgCl_2$ at pH8;

This was then treated with benzonase in 0.5 MTris/HCl, 1 mM $MgCl_2$ at pH8 and filtered through a 0.2 micron filter;

The resulting composition was subjected to strong anion-exchange chromatography employing Source 15Q resin using an elution buffer of 20 mM Tris, 1 mM MgCl2, 250 mM (0.25 M) NaCl at pH8;

This purified composition was concentrated and put into a final isotonic buffer using diafiltration.

Anion exchange chromatography is a process that separates substances based on their charges using an ion-exchange resin containing positively charged groups, such as diethyl-aminoethyl groups (DEAE). In the case of adenovirus production, anion exchange chromatography is used to purify adenoviruses from proteins in the host cells (host cell proteins or HCP) which are negatively charged at higher pH levels. Two stage ion-exchange chromatography is known form Brument et al, Molecular Therapy Vol. 6, No. 5, November 2002.

However, the present inventors have found that group B adenoviruses, such as Ad11 are not adequately separated from host cell proteins by anion exchange chromatography. FIG. 1A shows the retention time of Ad11 virus and Ad5 virus when analysed by anion exchange chromatography. These viruses have very different retention times of about 10 vs 15 on the x-axis. FIG. 1B shows that the Ad11-type viruses such as EnAd, elute with the host cell proteins using anion-exchange chromatography. Thus, although ion-exchange chromatography is currently the gold standard for adenovirus purification, it is not effective for group B viruses, for example Ad11-type viruses, such as EnAd because these viruses behave differently from group C viruses, such as Ad5.

The state of the art for work in the field of GMP manufacture of adenoviruses has primarily been performed on Ad5, i.e. a group C adenovirus.

The present inventors have found optimal conditions and processes for the purification of adenoviruses differs depending on the adenovirus group. Adenoviruses are grouped based on DNA homology and/or their hexon, fibre and capsid properties in chromatographic analysis.

Developing a successful recombinant adenoviral purification process requires a detailed understanding of the recombinant virus, such as the interaction between the host cell line and the virus. Essentially the process requires adaptation depending on the particular group of viruses.

Surprisingly the present inventors have found that group B adenoviruses, for example Ad11-type adenoviruses, such as EnAd can purified away from host cell proteins using essentially a one diafiltration step employing a high concentration of salt in the buffer. This has not been possible using the standard prior art processes. In embodiments it is possible to completely omit ion-exchange chromatography from the process.

Accordingly, there is a need for an improved purification process specifically tailored for the production of Group B adenoviruses.

SUMMARY OF THE INVENTION

Surprisingly, the present inventors have established that group B adenoviral vectors can be purified by a process that significantly reduces the levels of contaminating host cell proteins in the final product The present disclosure is described in the following paragraphs:

1. A method for purifying a replication competent group B adenovirus from host cell proteins, comprising a purification step of:
   subjecting a composition comprising said group B adenovirus to diafiltration employing a diafiltration-buffer with a conductivity of at least 180 $mScm^{-1}$, for example a conductivity of 190, 200, 210, 220, 230, 240, 250, 260, 270, 280, or 290 $mScm^{-1}$.
2. A method according to paragraph 1, wherein the conductivity is provided by a strong electrolyte.
3. A method according to paragraph 2, wherein the electrolyte is a salt, such as an ionic salt (in particular a salt that is fully soluble and highly dissociated in water).
4. A method for purifying a replication competent group B adenovirus from host cell proteins, comprising a purification step of:

subjecting a composition comprising said group B adenovirus to diafiltration employing a diafiltration-buffer with a high salt concentration, wherein said salt concentration is at least 2M, for example in the range 2.5M to 5.5M, such as 3M, 3.5M, 4M, 4.5M or 5M, in particular 4M, 4.1M, 4.2 m, 4.3M, 4.4M, 4.5M, 4.6M, 4.7M, 4.8M or 4.9M, more specifically 4.3M, e.g. with a conductivity of at least 180 $mScm^{-1}$, such as a conductivity of 190, 200, 210, 220, 230, 240, 250, 260, 270, 280, or 290 $mScm^{-1}$.

5. The method according to any one of paragraphs 3 or 4, wherein the buffer comprises a salt selected from a chloride salt (for example with cation selected from Li, Na, Mg, K, Ca, Cs, and $NH_4$), a sulfate salt, and any fully soluble and dissociated in water combinations thereof.

6. The method according to any one of paragraphs 3 or 5, wherein the salt in the diafiltration-buffer comprises one or more of the following: an alkaline earth metal salt (such a NaCl, KCl, and $MgCl_2$), sodium acetate, Tris, Bis-Tris, $NaH_2PO_4$, for example NaCl or KCl, in particular NaCl.

7. The method according to any one of paragraphs 1 to 6, wherein the diafiltration-buffer is selected from: meglumine buffer, Gly-NaCl buffer, TRIS buffer.

8. The method according to paragraph 7, wherein the diafiltration-buffer comprises HEPES, for example at least 10, 20, 30, 40, 50, 60 or 70 mM HEPES, in particular 50 mM HEPES.

9. The method according to any one of the preceding paragraphs, wherein the diafiltration-filtration buffer is at a pH in the range 7 to 9.8, for example 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, such as pH 7.5.

10. The method according to any one of paragraphs 1 to 10, wherein the diafiltration employs a 500 kDa MWCO ultrafiltration membrane, for example at least 300 KDa or greater.

11. The method according to any one of paragraphs 1 to 10, wherein the diafiltration has a flow rate of 1 to 3 $m^2/s$, for example 1.1, 1.2, 1.3, 1.4, 1.5, 1.6, 1.7, 1.8, 1.9, 2.0 $m^2/s$.

12. The method according to any one of paragraphs 1 to 11, wherein the diafiltration is a pressure independent regime.

13. The method according to any one of the preceding paragraphs, wherein the diafiltration is carried out employing a hollow fibre cartridge or flat membrane cassette filter.

14. The method according to paragraph 13, wherein the TFF is performed using a consistent volume method.

15. The method according to any one of the preceding paragraphs, wherein the diafiltration is performed using at least 8 diavolumes of high salt diafiltration-buffer, such as 11, 12, 13, 14, 15, 16, 17, 18 diavolumes, for example 11, 12, 13, 14, or 15 diavolumes, such as 12 diavolumes.

16. The method according to any one of the preceding paragraphs, wherein the diafiltration process comprises two steps (i.e. a first and second step).

17. The method of paragraph 16, wherein a first step of the process is diafiltration with the high conductivity diafiltration-buffer.

18. The method according to paragraph 16 or 17, wherein a second step of the process is diafiltration with the final formulation buffer.

19. The method according to paragraph 18, wherein the final formulation buffer comprises meglumine buffer, Glycine buffer, TRIS buffer, HEPES.

20. The method according to paragraph 19, wherein the final formulation buffer comprises HEPES, such as 5 mM HEPES.

21. The method according to any one of paragraphs 18 to 20, wherein the final formulation buffer comprises glycerol, for example 20% m/v glycerol.

22. The method according to paragraph 20 or 21, wherein the final formulation buffer consists of 5 mM HEPES and 20% m/V glycerol.

23. The method according to any one of paragraphs 16 to 22, wherein the second dilfiltration step is performed using at least 8 diavolumes of final formulation buffer, such as 11, 12, 13, 14, 15, 16, 17, 18 diavolumes, for example 15 diavolumes.

24. The method according to any one of paragraphs 1 to 23, wherein only one diafiltration buffer is employed.

25. The method according to any one of paragraphs 16 to 24, wherein the first diafiltration step sequentially employs multiple diafiltration-buffers.

26. The method according to paragraph 25, wherein 2, 3 or 4 diafiltration-buffers are employed, such as 2 diafiltration-buffers are employed.

27. The method according to paragraph 26, wherein one of the multiple diafiltration-buffers employed is 1M NaCl, 50 Mm HEPES, 1.0% m/V Tween 20, 1.0% m/V glycerol at pH 7.5.

28. The method according to any one of paragraph 18 to 27, wherein the pH of the final formulation buffer is in the range 7 to 9.8, for example 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, such as pH 7.5.

29. The method according to any one of the preceding paragraphs, comprising a further purification step comprising subjecting the composition of adenovirus to a chromatography purification.

30. The method according to paragraph 29, wherein the chromatography purification step is prior to the diafiltration.

31. The method according to paragraph 29, wherein the chromatography purification step is after the diafiltration step.

32. The method according to any one of paragraphs 29 to 31, wherein the chromatography step employs ion-exchange chromatography, for example anion exchange chromatography.

33. The method according to paragraph 32, wherein the anion exchange chromatography utilizes DEAE, TMAE, QAE or PEI.

34. The method according to any one of paragraphs 29 to 33, wherein the chromatography employs a Sartobind® IEX membrane absorber capsule.

35. The method according to paragraph 34, wherein the elution-buffer employed is 450 mM NaCl, 50 mM HEPES, 1.0% m/V Tween 20, at pH 7.5.

36. The method according to any one of paragraphs 29 to 35, wherein a high performance liquid chromatography is employed, for example CIMQA IEX2.

37. The method according paragraph 36, wherein the elution-buffer employed is 400 mM NaCl, 50 mM Tris, 2 Mm $MgCl_2$, 5% glycerol, at pH 7.8.

38. The method according to any one of paragraphs 1 to 37, wherein all the adenovirus purification steps to prepare the final adenovirus formulation are filtration steps.

39. The method according to any one of paragraphs 1 to 28 and 38, wherein the adenovirus purification steps do not employ chromatography.

40. The method according to any one of paragraphs 1 to 39, which comprises a pre-step of lysing the host cells in which adenovirus was replicated in to obtain a crude cell lysate.

18. The method according to paragraph 17, where the lysis step employs a lysis buffer.

19. The method of paragraph 18, wherein the lysis buffers comprises at least 10% surfactant 43. The method according to paragraph 42, where the surfactant is a non-ionic surfactant, such as Tween-20.

44. The method according to any one of paragraphs 41 to 43, which further comprises a salt at a concentration in the range 10 to 50 mM, such as 20, 30 or 40 mM, in particular 20 mM.

45. The method according to any one of paragraphs 41 to 44, wherein the lysis buffer comprises meglumine buffer, Glycine buffer, TRIS buffer, HEPES.

46. The method according to paragraph 45, wherein the lysis buffer comprises HEPES.

47. The method according to paragraph 46, wherein the HEPES concentration is in the range 4.5M to 5.5M, such as 5M.

48. The method according to any one of paragraphs 41 to 47, wherein the lysis buffer is in the pH range 7.75 to 8.25, for example pH 8.

49. The method according to any one of paragraphs 40 to 48, wherein an endonuclease, for example Benzonase, is added to the crude cell lysate.

50. The method according to paragraph 49, wherein the adenovirus is transferred into an inactivation buffer.

51. The method according to paragraph 50, wherein the inactivation buffer comprises a high salt content, for example in the range 0.75 to 1.25M, such as 1M.

52. The method according to paragraph 50 or 51, wherein the inactivation buffer has a pH in the range 7.25 to 7.75, such as pH 7.5.

53. The method according to any one of paragraphs 40 to 52, wherein the crude cell lysate after addition of an endonuclease is filtered to clarify the adenovirus composition.

54. The method according to paragraph 53, wherein the filter is a depth filter.

55. The method according to paragraph 53 or 54, wherein depth filter employed has a specification of 4 to 2 μm, for example a CE35 (from Merck Millipore).

56. The method according to any one of paragraphs 53 to 55, wherein a second filter is employed in the clarification.

57. The method according to paragraph 56, wherein the second filter is a depth filter.

58. The method according to paragraph 57, wherein the depth filter employed has a specification of 1 to 0.4 μm.

59. The method according to any one of paragraphs 1 to 58, which comprises a filtration step comprising passing the adenovirus composition through a 0.2 μm filter to.

60. The method according to paragraph 59, wherein the filtration step is preformed prior to the diafiltration step.

61. The method according to any one of the preceding paragraphs, wherein the group B adenovirus comprises a sequence of formula (I):

$$5'ITR\text{-}B_1\text{-}B_A\text{-}B_2\text{-}B_X\text{-}B_B\text{-}B_Y\text{-}B_3\text{-}3'ITR$$

wherein:

- $B_1$ is bond or comprises: E1A, E1B or E1A-E1B;
- $B_A$ comprises-E2B-L1-L2-L3-E2A-L4;
- $B_2$ is a bond or comprises: E3;
- $B_X$ is a bond or a DNA sequence comprising: a restriction site, one or more transgenes or both;
- $B_B$ comprises L5;
- $B_Y$ is a bond or a DNA sequence comprising: a restriction site, one or more transgenes or both;
- $B_3$ is a bond or comprises: E4;

wherein at least one of $B_X$ or $B_Y$ is not a bond.

62. The method according to paragraph 61, wherein $B_X$ comprises a transgene or transgene cassette.

63. The method according to paragraph 61, wherein $B_X$ is a bond.

64. The method according to any one of paragraphs 61 to 63, wherein $B_Y$ comprises a transgene or transgene cassette.

65. The method according to any one of paragraphs 61 to 64, wherein the one or more transgenes or transgene cassette is under the control of an endogenous or exogenous promoter, such as an endogenous promotor.

66. The method according to paragraph 65, wherein the transgene cassette is under the control of an endogenous promoter selected from the group consisting of E4 and major late promoter, such as the major late promoter.

67. The method according to any one of paragraphs 61 to 66, wherein the transgene cassette further comprises a regulatory element independently selected from:

a. a splice acceptor sequence,
b. an internal ribosome entry sequence or a high self-cleavage efficiency 2A peptide,
c. a Kozak sequence, and
d. combinations thereof.

68. The method according to paragraph 67, wherein the transgene cassette comprises a Kozak sequence is at the start of the protein coding sequence.

69. The method according to any one of paragraphs 61 to 68, wherein the transgene cassette encodes a high self-cleavage efficiency 2A peptide.

70. The method according to any one of paragraphs 61 to 69, wherein the transgene cassette further comprises a polyadenylation sequence.

71. The method according to any one of paragraphs 61 to 70, wherein the transgene cassette further comprises a restriction site at the 3'end of the DNA sequence and/or at the 5'end of the DNA sequence.

72. The method according to any of paragraphs 61 to 71, wherein at least one transgene cassette encodes monocistronic mRNA.

73. The method according to any one of paragraphs 61 to 72, wherein at least one transgene cassette encodes a polycistronic mRNA.

74. The method according to any one of paragraphs 61 to 73, wherein the transgene encodes an RNAi sequence, a peptide or a protein.

75. The method according to paragraph 74, wherein the transgene encodes an antibody or binding fragment thereof.

76. The method according to paragraph 75, wherein the antibody or binding fragment thereof is specific to OX40, OX40 ligand, CD27, CD28, CD30, CD40, CD40 ligand, CD70, CD137, GITR, 4-1BB, ICOS, ICOS ligand, CTLA-4, PD-1, PD-L1, PD-L2, VISTA, B7-H3, B7-H4, HVEM, ILT-2, ILT-3, ILT-4, TIM-3, LAG-3, BTLA, LIGHT, CD160, CTLA-4, PD-1, PD-L1, PD-L2, for example CD40 and CD40 ligand.

77. The method according to any one of paragraphs 61 to 76, wherein the transgene encodes a cytokine independently selected from the group comprising IL-1α, IL-1β, IL-6, IL-9, IL-12, IL-13, IL-17, IL-18, IL-22, IL-23, IL-24, IL-25, IL-26, IL-27, IL-33, IL-35, IL-2, IL-4, IL-5, IL-7, IL-10, IL-15, IL-21, IL-25, IL-1RA, IFNα, IFNβ, IFNγ, TNFα, TGFβ, lymphotoxin α (LTA) and GM-CSF, for example IL-12, IL-18, IL-22, IL-7, IL-15, IL-21, IFNγ, TNFα, TGFα and lymphotoxin α (LTA).

78. The method according to any one of paragraphs 61 to 77, wherein the transgene encodes a chemokine independently selected from the group comprising IL-8, CCL5, CCL17, CCL20, CCL22, CXCL9, CXCL10, CXCL11, CXCL13, CXCL12, CCL2, CCL19, CCL21, CXCR2, CCR2, CCR4, CCR5, CCR6, CCR7, CCR8, CXCR3, CXCR4, CXCR5 and CRTH2, for example CCL5, CXCL9, CXCL12, CCL2, CCL19, CCL21, CXCR2, CCR2, CCR4 and CXCR4 or a receptor thereof.

79. The method according to any one of paragraphs 61 to 78, wherein the transgene is a reporter gene, for example sodium iodide symporter, intracellular metalloproteins, HSV1-tk, GFPs, luciferase or oestrogen receptor, for example sodium iodide symporter.

80. The method according to any one of paragraphs 1 to 79, wherein the E4orf4 region of the adenovirus is non-functional, for example fully deleted, partially deleted or truncated.

81. The method according to any one of paragraphs 1 to 80, wherein the E2B region of the adenovirus is chimeric, for example wherein the E2B region comprises a nucleic acid sequence derived from a first adenoviral serotype and a nucleic acid sequence derived from a second distinct adenoviral serotype; wherein said first and second serotypes are each selected from the adenoviral subgroups B, C, D, E, or F.

82. The method according to any one of paragraphs 1 to 81, wherein the adenovirus is Ad11.

83. The method according to any one of paragraphs 1 to 81, wherein the adenovirus is chimeric EnAd.

84. The method according to any one of paragraphs 1 to 83, wherein the adenovirus is replication capable, for example replication competent 85. The method according to any one of paragraphs 1 to 83, wherein the adenovirus is replication deficient.

86. An adenovirus composition obtained or obtainable from the method according to any one of paragraphs 1 to 85.

87. An adenovirus composition according to paragraph 86, for use in treatment, in particular for use in the treatment of cancer.

88. An adenovirus composition according to paragraph 86, for use in the manufacture of a medicament for use in the treatment of cancer.

89. A method of treatment comprising the step of administering a therapeutically effective amount of an adenovirus composition defined in paragraph 86.

DETAILED DESCRIPTION OF THE DISCLOSURE

Figure 1A:
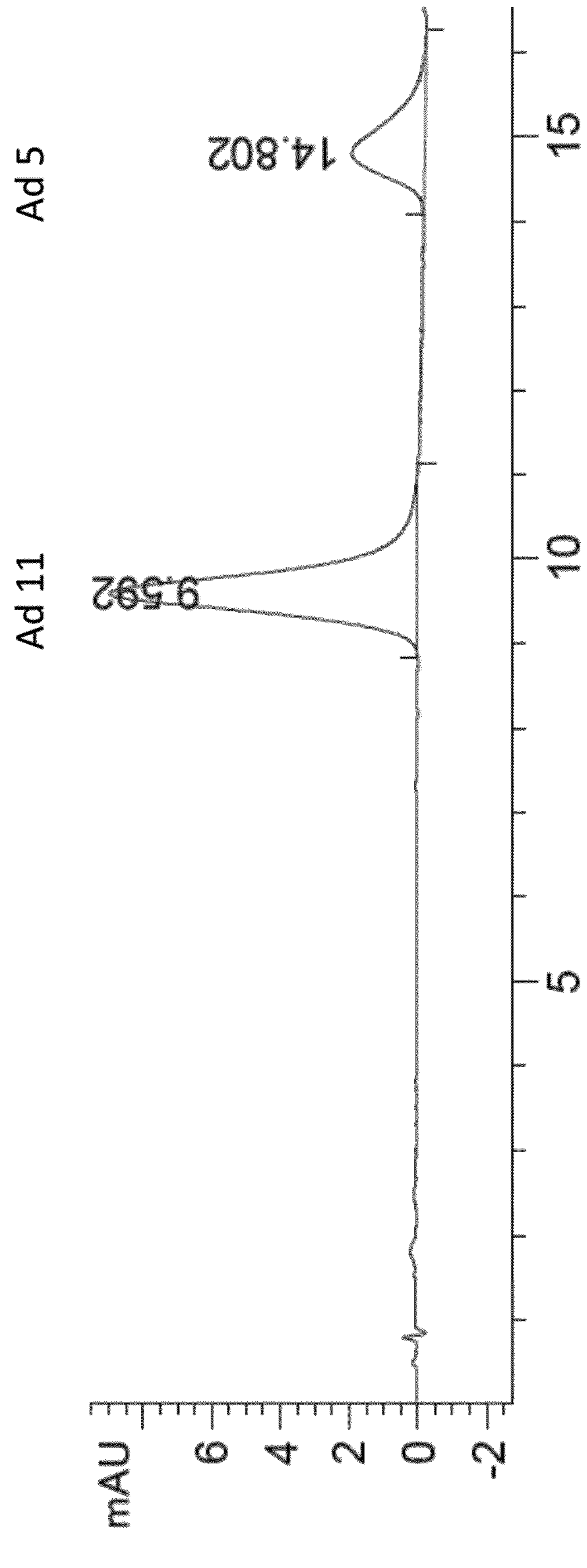
FIG. 1A is a chromatogram showing the analytical separation of Adenovirus 5 (Ad5) and Adenovirus 11 (Ad11) by anion exchange chromatography.
Figure 1B:
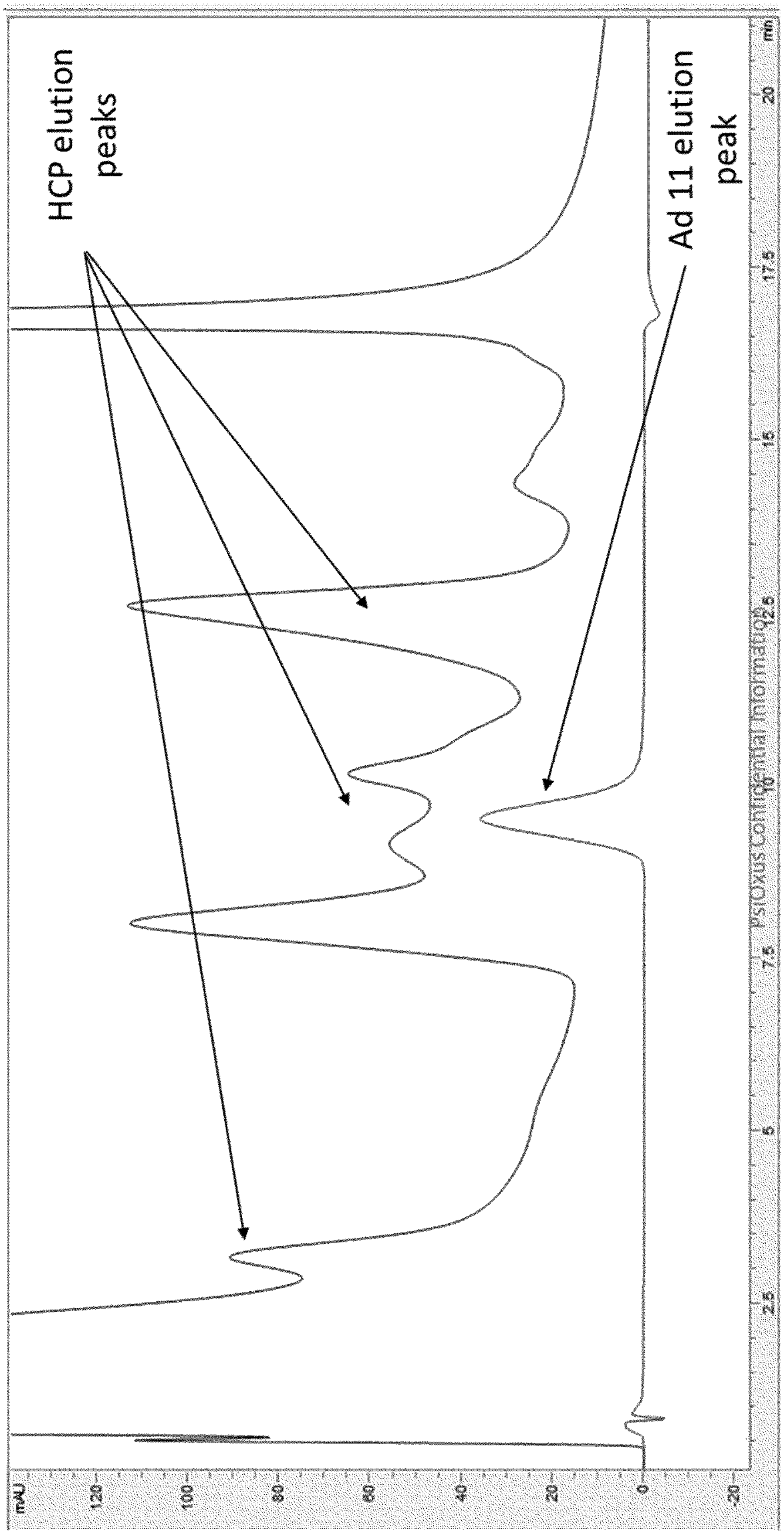
FIG. 1B is a chromatogram showing that Ad11 is not separated from the host cell proteins by anion exchange chromatography alone.
Figure 2A:
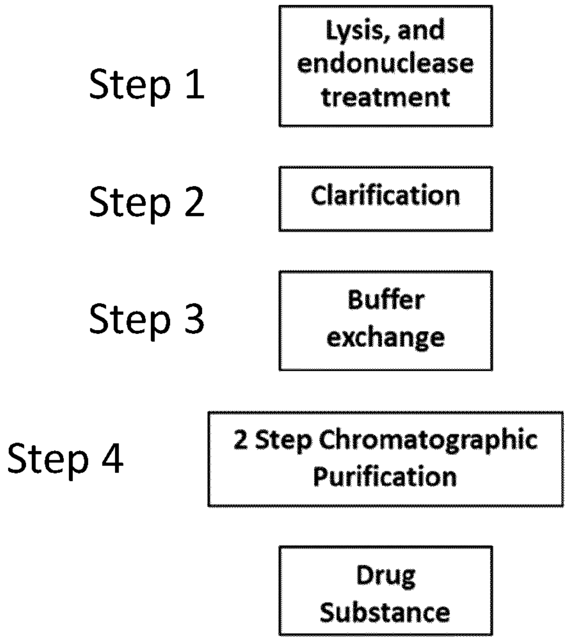
FIG. 2 (A) is a flow diagram depicting a standard purification process for an adenovirus (B) is a flow diagram depicting a modified purification process of the present disclosure for group B adenovirus vectors FIG. 3 Shows the technical details for the modified process shown in FIG. 2B FIG. 4 Shows a flow diagram depicting a single-step purification process of the present disclosure for adenovirus vectors.
Figure 2B:
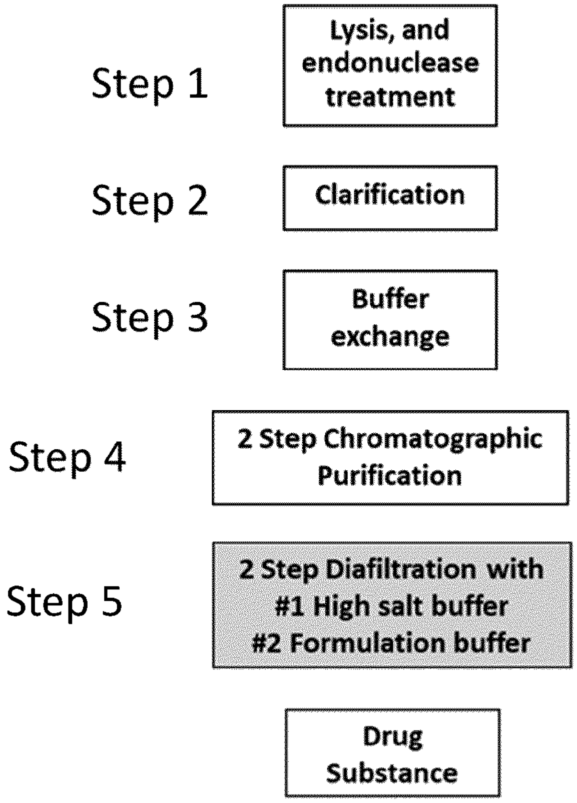

By reference to the steps defined in FIG. 2B and Example 2, the process may be performed in any suitable order, for example may comprise or consist of the following steps:

Step 1, step 2, and step 5; or Step 1, step 2, step 5, and step 4*a*; or Step 1, step 2, step 5, and step 4*b*; or Step 1, step 2, step 5, step 4*a* and step 4*b*; or Step 1, step 2, step 3, step 4*a* and step 5; or Step 1, step 2, step 3, step 4*b* and step 5; or Step 1, step 2, step 3, step 4*a*, step 4*b* and step 5.

Ultrafiltration as used herein refers to a separation process that uses membranes to separate components in a liquid composition based upon particle size differences. The method uses pressure and/or concentration gradients to separate components. By controlling the pore size of the membranes, components in the composition can be either retained or allowed to pass through the membrane.

Suitable membranes include 500 kDa MWCO ultrafiltration membrane, for example which retains molecules at least 300 KDa and greater.

Diafiltration or buffer exchange as used herein refers to an ultrafiltration process typically used for desalting and solvent-exchange of proteins. Diafiltration in the context of the present disclosure is used to wash microspecies, such as host cell proteins and other unwanted contaminants from the culture media used to produce adenoviruses, thereby generating a purified solution of the retained species, i.e. the adenoviruses.

Diafiltration can be performed using either continuous diafiltration also known as the consistent volume method, or discontinuous diafiltration. In the consistent volume method, diafiltration buffer is added to sample feed reservoir at the same rate as filtrate is being generated. This means that the volume of solution in the sample feed-reservoir remains the same, but molecules that are small enough to pass through the membrane, such as the host cell proteins, are washed away. In comparison, in the discontinuous method, the sample solution is first diluted and then concentrated back to the starting volume. This process is repeated until the required concentration of small molecules remaining in the reservoir is reached, i.e. until the desired purity of the sample solution is achieved. Continuous diafiltration typically requires less filtrate volume to achieve the same degree of reduction in “drug” molecule concentration of the starting solution, as compared to discontinuous diafiltration.

Tangential flow filtration (TFF) or crossflow filtration as used herein refers to an ultrafiltration technique wherein the feed stream passes parallel to the membrane face as one portion passes through the membrane (permeate), while the remainder (retentate) is recirculated back to the feed reservoir. This is in contrast to direct flow filtration (DFF), whereby the feed stream is fed perpendicular to the membrane face and attempts to pass all of the fluid through the membrane. In the TFF method the flow of sample solution is across the membrane surface, which sweeps away aggregating molecules that may form a membrane-clogging gel, whilst allowing molecules smaller than the membrane pores to move toward and through the membrane. Thus, the TFF method tends to be faster and more efficient than the DFF method for size separation.

Diavolume, as used herein, is a measure of the extent of washing that has been performed during a diafiltration step. It is based on the volume of diafiltration buffer introduced into the unit operation compared to the retentate volume.

Diafiltration-buffer, as employed herein, refers to a biological buffer employed in the diafiltration process.

Elution buffer, unless the context indicates otherwise refers to a buffer employed in a chromatography step.

Lysis buffer as employed herein refers to a buffer suitable to lysing the host cells in which the virus is grown, and will generally contain a surfactant.

Final formulation buffer as employed herein refers a buffer, which under appropriate conditions is suitable for storing the adenovirus in and/or suitable for administration to a human.

Concentration factor as employed here refers to where the volume of a given solute is reduced by, to increase the concentration by a factor(s) or fold increase.

Biological buffer (also referred to as simply a buffer) as used herein refers to a buffer suitable for suspending or storing viruses, without negatively affecting the structural integrity of the adenoviruses or their ability to replicate. Most biological buffers in use today were developed by NE Good and his research team (Good et al. 1966, Good & Izawa 1972, Ferguson et al. 1980; "Good buffers") and include N-substituted taurine or glycine buffers. Table 1 below lists some commonly used biological buffers. This list is not exhaustive and other buffers will also be known to the skilled addressee.

TABLE 1 list of common biological buffers

| Trivial name | Name |
|---|---|
| ACES | N-(2-Acetamido)-aminoethanesulfonic acid |
| Acetate | Salt of acetic acid |
| ADA | N-(2-Acetamido)-iminodiacetic acid |
| AES | 2-Aminoethanesulfonic acid, Taurine |
| Ammonia | — |
| AMP | 2-Amino-2-methyl-1-propanol |
| AMPD | 2-Amino-2-methyl-1,3-propanediol, Ammediol |
| AMPSO | N-(1,1-Dimethyl-2-hydroxyethyl)-3-amino-2-hydroxypropanesulfonic acid |
| BES | N,N-Bis-(2-hydroxyethyl)-2-aminoethanesulfonic acid |
| Bicarbonate | Sodium hydrogen carbonate |
| Bicine | N,N'-Bis(2-hydroxyethyl)-glycine |
| BIS-Tris | [Bis-(2-hydroxyethyl)-imino]-tris-(hydroxymethylmethane) |
| BIS-Tris-Propane | 1,3-Bis[tris(hydroxymethyl)-methylamino]propane |
| Boric acid | — |
| Cacodylate | Dimethylarsinic acid |
| CAPS | 3-(Cyclohexylamino)-propanesulfonic acid |
| CAPSO | 3-(Cyclohexylamino)-2-hydroxy-1-propanesulfonic acid |
| Carbonate | Sodium carbonate |
| CHES | Cyclohexylaminoethanesulfonic acid |
| Citrate | Salt of citric acid |
| DIPSO | 3-[N-Bis(hydroxyethyl)amino]-2-hydroxypropanesulfonic acid |
| Formate | Salt of formic acid |
| Glycine | — |
| Glycylglycine | — |
| HEPES | N-(2-Hydroxyethyl)-piperazine-N'-ethanesulfonic acid |
| HEPPS, EPPS | N-(2-Hydroxyethyl)-piperazine-N'-3-propanesulfonic acid |
| HEPPSO | N-(2-Hydroxyethyl)-piperazine-N'-2-hydroxypropanesulfonic acid |
| Imidazole | — |
| Malate | Salt of malic acid |
| Maleate | Salt of maleic acid |
| MES | 2-(N-Morpholino)-ethanesulfonic acid |
| MOPS | 3-(N-Morpholino)-propanesulfonic acid |
| MOPSO | 3-(N-Morpholino)-2-hydroxypropanesulfonic acid |
| Phosphate | Salt of phosphoric acid |
| PIPES | Piperazine-N,N'-bis(2-ethanesulfonic acid) |
| POPSO | Piperazine-N,N'-bis(2-hydroxypropanesulfonic acid) |
| Pyridine | — |
| Succinate | Salt of succinic acid |
| TAPS | 3-{[Tris(hydroxymethyl)-methyl]-amino}-propanesulfonic acid |
| TAPSO | 3-[N-Tris(hydroxymethyl)-methylamino]-2-hydroxypropanesulfonic acid |
| Taurine | 2-Aminoethanesulfonic acid, AES |
| TEA | Triethanolamine |
| TES | 2-[Tris(hydroxymethyl)-methylamino]-ethanesulfonic acid |
| Tricine | N-[Tris(hydroxymethyl)-methyl]-glycine |
| Tris | Tris(hydroxymethyl)-aminomethane |

Strong electrolyte, as employed herein, refers to substances which when dissolved in water break up into cations and anions. Strong electrolytes ionize completely and fall into three categories: strong acids, strong bases and salts.

Strong acids include HCl, HBr, HI, $HNO_3$, $HClO_3$ and $H_2SO_4$.

Strong bases include NaOH, KOH, LiOH, $Ba(OH)_2$ and $Ca(OH)_2$.

Salt as used herein refers to any salt suitable for use as a diafiltration buffer which is therefore a buffer suitable for biological applications, in particular for use as a biological buffer. Examples of such salts are known to the skilled person and include but are not limited to NaCl, Tris, Bis-Tris and $NaH_2PO_4$.

Conductivity is generally measured by determining the resistance of a liquid between two electrodes, which are a fixed distance apart Conductivity meters are available from Omega and Baumer.

Adenovirus as employed herein generally refer to a replication competent adenovirus or replication deficient, for example a group B virus, in particular Ad11, such as Ad11p (including viruses derived thereform) unless the context indicates otherwise. In some instances, it may be employed to refer only to replication competent viruses and this will be clear from the context Subgroup B (group B or type B) as employed herein refers to viruses with at least the fibre and hexon from a group B adenovirus, for example the fibre, hexon and penton, or for example the whole capsid from a group B virus, such as substantially the whole genome from a group B virus.

Enadenotucirev (EnAd) is a chimeric oncolytic adenovirus, formerly known as ColoAd1 (WO2005/118825), with fibre, penton and hexon from Ad11p, hence it is a group B virus derived from Ad11p. It has a chimeric E2B region, which comprises DNA from Ad11p and Ad3. Almost all of the E3 region and part of the E4 region (E4orf4) is deleted in EnAd.

EnAd as employed herein also includes the virus which encodes one or more transgenes.

A process for the manufacture of an adenovirus as employed herein is intended to refer to a process wherein the virus is replicated and thus the number of viral particles is increased. In particular the manufacturing is to provide sufficient numbers of viral particles to formulate a therapeutic product, for example in the range $1\text{-}9\times10^5$ to $1\text{-}9\times10^{20}$ or more particles may be produced, such as in the range of $1\text{-}9\times10^8$ to $1\text{-}9\times10^{15}$ viral particles, in particular 1 to $9\times10^{10}$ or $1\text{-}9\times10^{15}$ viral particles may be produced from a 10 L batch.

A process for purify a group B adenovirus as employed here requires the process be fit for the intended purpose. In one embodiment the virus that is purified by the process is Ad11, such as EnAd.

Part of the E3 region is deleted (partly deleted in the E3 region) as employed herein refers to at least part, for example in the range 1 to 99% of the E3 region is deleted, such as 2, 3, 4, 5, 6, 7, 8, 9, 10, 15, 20, 25, 30, 35, 40, 45, 50, 55, 60, 65, 70, 75, 80, 85, 90, 91, 92, 93, 94 95, 96, 97 or 98% deleted, for example in a coding and/or non-coding region of the gene.

Completely deleted (also referred to herein as wholly deleted) in the E3 region means the coding part of the gene is completed deleted. In one embodiment the coding and non-coding part of the gene is completely deleted.

E3 as employed herein refers to the DNA sequence encoding part or all of an adenovirus E3 region (i.e. protein/polypeptide), it may be mutated such that the protein encoded by the E3 gene has conservative or non-conservative amino acid changes, such that it has the same function as wild-type (the corresponding unmutated protein); increased function in comparison to wild-type protein; decreased function, such as no function in comparison to wild-type protein or has a new function in comparison to wild-type protein or a combination of the same, as appropriate.

The viruses of the present disclosure are not partly deleted in the E4 region.

In one embodiment the Eorf4 is deleted.

"Part of the E4 region is deleted" (partly deleted in the E4 region) as employed herein means that at least part, for example in the range 1 to 99% of the E4 region is deleted, such as 2, 3, 4, 5, 6, 7, 8, 9, 10, 15, 20, 25, 30, 35, 40, 45, 50, 55, 60, 65, 70, 75, 80, 85, 90, 91, 92, 93, 94 95, 96, 97 or 98% deleted.

Completely present in the E4 region means the E4 is 100% present i.e. nothing is removed. Having said that the gene may be: mutated wherein up to 10% of the base pairs are replaced (but not deleted); or be interrupted, for example the E4 region may be interrupted by a transgene. Thus 100% complete as employed herein means 100% present in the relevant location in the genome, however the gene many be contiguous or non-contiguous.

Completely deleted (also referred to herein as wholly deleted) in the E4 region means the coding part of the gene is completed deleted. In one embodiment the coding and non-coding part of the gene is deleted.

E4 as employed herein refers to the DNA sequence encoding an adenovirus E4 region (i.e. polypeptide/protein region), which may be mutated such that the protein encoded by the E4 gene has conservative or non-conservative amino acid changes, and has the same function as wild-type (the corresponding non-mutated protein); increased function in comparison to wild-type protein; decreased function, such as no function in comparison to wild-type protein or has a new function in comparison to wild-type protein or a combination of the same, as appropriate.

The E4 region may have some function or functions relevant to viral replication and thus modifications, such as deletion of the E4 region may impact on a virus life-cycle and replication, for example such that a packaging cell may be required for replication.

"Derived from" as employed herein refers to, for example where a DNA fragment is taken from an adenovirus or corresponds to a sequence originally found in an adenovirus. This language is not intended to limit how the sequence was obtained, for example a sequence employed in a virus according to the present disclosure may be synthesised.

In one embodiment the derivative has 100% sequence identity over its full length to the original DNA sequence, i.e. the original DNA sequence may be part of all of the relevant adenovirus. In one example the DNA sequence encodes the fibre and hexon, such as the capsid proteins.

In one embodiment the derivative has 95, 96, 97, 98 or 99% identity or similarity to the original DNA sequence.

In one embodiment the derivative hybridises under stringent conditions to the original DNA sequence.

As used herein, "stringency" typically occurs in a range from about Tm (melting temperature) −50° C. (5° below the Tm of the probe) to about 20° C. to 25° C. below Tm. As will be understood by those of skill in the art, a stringent hybridization can be used to identify or detect identical polynucleotide sequences or to identify or detect similar or related polynucleotide sequences. As herein used, the term "stringent conditions" means hybridization will generally occur if there is at least 95%, such as at least 97% identity between the sequences.

As used herein, "hybridization" as used herein, shall include "any process by which a polynucleotide strand joins (aligns) with a complementary strand through base pairing" (Coombs, J., *Dictionary of Biotechnology*, Stockton Press, New York, N.Y., 1994).

In one embodiment viruses of the present disclosure further comprise a transgene.

In one embodiment the lack of adherence to the cells may be related to the hexon and fibre of the virus.

In one embodiment the adenovirus employed in the present disclosure is oncolytic.

Oncolytic viruses are those which preferentially infect cancer cells and hasten cell death, for example by lysis of same, or selectively replicate in the cancer cells. Viruses which preferentially infect cancer cells are viruses which show a higher rate of infecting cancer cells when compared to normal healthy cells.

In one embodiment the virus of the present disclosure is chimeric, for example comprises genomic sequence from at least two adenovirus subgroups (excluding subgroup A which is thought to be cancer causing). In one embodiment the chimeric adenoviruses of the present disclosure are not chimeric in the E2B region.

An adenovirus, such as a replication competent group B adenovirus can be evaluated for its preference for a specific tumor type by examination of its lytic potential in a panel of tumor cells, for example colon tumor cell lines include HT-29, DLD-1, LS174T, L51034, SW403, HCT116, SW48, and Colo320DM. Any available colon tumor cell lines would be equally useful for such an evaluation.

Prostate cell lines include DU145 and PC-3 cells. Pancreatic cell lines include Panc-1 cells. Breast tumor cell lines include MDA231 cell line and ovarian cell lines include the OVCAR-3 cell line. Hemopoietic cell lines include, but are not limited to, the Raji and Daudi B-lymphoid cells, K562 erythroblastoid cells, U937 myeloid cells, and HSB2 T-lymphoid cells. Other available tumor cell lines are equally useful.

In one embodiment a virus of the present disclosure is oncolytic. Oncolytic viruses including those which are non-chimeric (i.e. oncolytic viruses may be chimeric or non-chimeric), for example Ad11, such as Ad11p can similarly be evaluated in these cell lines and has oncolytic activity.

Viruses which selectively replicate in cancer cells are those which require a gene or protein which is upregulated in a cancer cell to replicate, such as a p53 gene.

In one embodiment the oncolytic virus of the present disclosure is apoptotic, that is hastens programmed cell death. In one embodiment the oncolytic virus of the present disclosure is cytolytic. The cytolytic activity of chimeric oncolytic adenoviruses of the disclosure can be determined in representative tumor cell lines and the data converted to a measurement of potency, for example with an adenovirus belonging to subgroup C, preferably Ad5, being used as a standard (i.e. given a potency of 1). A suitable method for determining cytolytic activity is an MTS assay (see Example 4, FIG. 2 of WO 2005/118825 incorporated herein by reference). In one embodiment the oncolytic adenovirus of the present disclosure causes cell necrosis.

In one embodiment the chimeric oncolytic virus has an enhanced therapeutic index for cancer cells. Therapeutic index" or "therapeutic window" refers to a number indicating the oncolytic potential of a given adenovirus which may be determined by dividing the potency of an oncolytic adenovirus of the present disclosure in a relevant cancer cell line divided by the potency of the same adenovirus in a normal (i.e. non-cancerous) cell line. In one embodiment the oncolytic virus has an enhanced therapeutic index in one or more cancer cells selected from the group comprising colon cancer cells, breast cancer cells, head and neck cancers, pancreatic cancer cells, ovarian cancer cells, hemopoietic tumor cells, leukemic cells, glioma cells, prostate cancer cells, lung cancer cells, melanoma cells, sarcoma cells, liver cancer cells, renal cancer cells, bladder cancer cells and metastatic cancer cells.

Group B viruses include Ad3, 7, 11, 14, 16, 21, 34, 35, 50 and 55.

The E2B region is a known region in adenoviruses and represents about 18% of the viral genome. It is thought to encode protein IVa2, DNA polymerase and terminal protein. In the Slobitski strain of Ad11 (referred to as Ad11p) these proteins are encoded at positions 5588-3964, 8435-5067 and 10342-8438 respectively in the genomic sequence and the E2B region runs from 10342-3950. The exact position of the E2B region may change in other serotypes but the function is conserved in all human adenovirus genomes examined to date as they all have the same general organisation.

In one embodiment the virus of the present disclosure, such as an oncolytic virus has a subgroup B hexon.

In one embodiment the virus has a hexon and fibre from a group B adenovirus, for example Ad11. In one embodiment the virus of the disclosure, such as an oncolytic virus has an Ad11 hexon, such as an A11p hexon. In one embodiment the virus of the disclosure, such as an oncolytic virus has a subgroup B fibre. In one the virus of the disclosure, such as an oncolytic virus has an Ad11 fibre, such as an A11p fibre. In one embodiment the virus of the disclosure, such as an oncolytic virus has fibre and hexon proteins from the same serotype, for example a subgroup B adenovirus, such as Ad11, in particular Ad11p.

In one embodiment the virus of the disclosure, such as an oncolytic virus has fibre, hexon and penton proteins from the same serotype, for example Ad11, in particular Ad11p, for example found at positions 30811-31788, 18254-21100 and 13682-15367 of the genomic sequence of the latter.

In one embodiment the virus of the virus of the present disclosure has an Ad11 capsid, for example an Ad11p capsid.

Mammalian cells in which the virus is cultured (and for example replicated) are cell derived from a mammal. In one embodiment the mammalian cells are selected from the group comprising HEK, CHO, COS-7, HeLa, Viro, A549, PerC6 and GMK, in particular HEK293.

In one embodiment the adenovirus is replication capable, for example replication competent.

Replication capable as employed herein is a adenovirus that can replicate in a host cell. In one embodiment replication capable encompasses replication competent and replication selective viruses.

Replication competent as employed herein is intended to mean an adenovirus that is capable of replicating in a human cell, such as a cancer cell, without any additional complementation to that required by wild-type viruses, for example without relying on defective cellular machinery. Replication competent viruses can be manufacture without the assistance of a complementary cell line encoding an essential viral protein, such as that encoded by the El region (also referred to as a packaging cell line) and virus capable of replicating without the assistance of a helper virus.

Replication selective or selective replication as employed herein is intended to mean an oncolytic virus that is able to replicate in cancer cells employing an element which is specific to said cancer cells or upregulated therein, for example defective cellular machinery, such as a p53 mutation, thereby allowing a degree of selectivity over healthy/normal cells.

In one embodiment the adenoviruses of the present disclosure are replication competent.

In one embodiment the adenoviruses of the present disclosure are replication deficient Replication deficient viruses require a packaging cell line to replicate. Packaging cell lines contain a gene or genes to complement those which are deficient in the virus.

In one embodiment the cells are grown in adherent or suspension culture, in particular a suspension culture.

Culturing mammalian cells, as employed herein, refers to the process where cells are grown under controlled conditions ex vivo. Suitable conditions are known to those in the art and may include temperatures such as 37° C. The $CO_2$ levels may need to be controlled, for example kept at a level of 5%. Details of the same are given in the text Culture of Animal Cells: A Manual of Basic Techniques and Specialised Applications Edition Six R. Ian Freshney, Basic Cell Culture (Practical Approach) Second Edition Edited by J. M. Davis.

Usually the cells will be cultured to generate sufficient numbers before infection with the adenovirus. These methods are known to those skilled in the art or are readily available in published protocols or the literature.

Generally the cells will be cultured on a commercial scale, for example 5 L, 10 L, 15 L, 20 L, 25 L, 30 L, 35 L, 40 L, 45 L, 50 L, 100 L, 200 L, 300 L, 400 L, 500 L, 600 L, 700 L, 800 L, 900, 1000 L or similar.

Media suitable for culturing mammalian cells include but are not limited to EX-CELL® media from Sigma-Aldrich, such as EX-CELL®293 serum free medium for HEK293 cells, EX-CELL® ACF CHO media serum free media for CHO cells, EX-CELL® 302 serum free media for CHO cells, EX-CELL CD hydrolysate fusion media supplement, from Lonza RMPI (such as RMPI 1640 with HEPES and L-glutamine, RMPI 1640 with or without L-glutamine, and RMPI 1640 with UltraGlutamine), MEM and DMEM, SFMII medium.

In one embodiment the medium is serum free. This is advantageous because it facilitates registration of the manufacturing process with the regulatory authorities.

The viruses of the present disclosure, such as oncolytic viruses have different properties to those of adenoviruses used as vectors such as Ad5, this includes the fact that they can be recovered from the medium without the need for cell lysis. Thus, whilst not wishing to be bound by theory, the viruses appear to have mechanisms to exit the cell.

In one embodiment the culturing period is in the range 30 to 100 hours, for example 35 to 70 hours, for example 40, 45, 50, 55, 60 or 65 hours post infection.

In one embodiment the culturing period is 65, 70, 75, 80, 85, 90, 95 hours or more.

In one embodiment the culturing period is in the range 60 to 96 hours.

In one embodiment the maximum total virus production is achieved at about 60 to 96 hours, for example 70 to 90 hours post-infection.

Culturing cells may employ a perfusion culture, fed batch culture, batch culture, a steady state culture, a continuous culture or a combination of one or more of the same as technically appropriate, in particular a perfusion culture.

In one embodiment the process is a perfusion process, for example a continuous perfusion process.

In one embodiment the culture process comprises one or more media changes. This may be beneficial for optimising cell growth, yield or similar. Where a medium change is employed, it may be necessary to recover virus particle from the media being changed. These particles can be combined with the main virus batch to ensure the yield of virus is optimised. Similar techniques may also be employed with the medium of a perfusion process to optimise virus recovery.

In one embodiment the culture process does not include a medium change step. This may be advantageous because no viral particles will be lost and therefore yield may be optimised.

In one embodiment the culture process comprises one or more cell additions or changes. Cell addition as employed herein refers to replenishing some or all of the cells and change refers to removing dead cells and adding new cells (not necessarily in that order).

In one embodiment the adenovirus during culture is at concentration in the range 20 to 150 particles per cell (ppc), such as 40 to 100 ppc, in particular 50 ppc.

Lower values of virus concentrations, such as less than 100 ppc, in particular 50 ppc may be advantageous because this may result in increased cell viability compared to cultures with higher virus concentrations, particularly when cell viability is measured before harvesting.

Low cell viability can result in cell lysis which may expose the cell to enzymes, which with time may attack the virus. However, in a dynamic process such as cell culturing a percentage, usually a small percentage of cells may be unviable. This does not generally cause significant problems in practice.

In one embodiment cell viability is around 80 to 95% during the process, for example at the 96 hour time point (i.e. 96 hours post-infection) when infected with virus, such as 83 to 90% viability.

In one embodiment cell viability is around 80 to 90% during the process, for example at the 96 hour time point (i.e. 96 hours post-infection) when infected with Ad11. For example 85% viability.

In one embodiment the medium and/or cells are supplements or replenished periodically.

In one embodiment the cells are harvested during the process, for example at a discrete time point or at time points or continuously.

In one embodiment harvesting the virus is performed at a time point selected from about 40, 46, 49, 64, 70, 73, 89 or 96 hours post infection or a combination thereof.

In one embodiment of the process the mammalian cells are infected with a starting concentration of virus of $1\text{-}9\times10^4$ vp/ml or greater, such as $1\text{-}9\times10^5$, $1\text{-}9\times10^6$, $1\text{-}9\times10^7$, $1\text{-}9\times10^8$, $1\text{-}9\times10^9$, in particular $1\text{-}5\times10^6$ vp/ml or $2.5\text{-}5\times10^8$ vp/ml.

In one embodiment of the process the mammalian cells are infected at a starting concentration of $1\times10^6$ cells/ml at about 1 to 200 ppc, for example 40 to 120 ppc, such as 50 ppc.

Ppc as employed herein refers to the number of viral particles per cell.

In one embodiment the process is run at about 35 to 39° C., for example 37° C.

In one embodiment the process run at about 4-6% $CO_2$, for example 5% $CO_2$.

In one embodiment the media containing the virus, such as the chimeric oncolytic viral particles is filtered to remove the cells and provide crude supernatant for further downstream processing. In one embodiment a tangential flow filter is employed.

In one embodiment medium is filtered employing Millipore's Millistak+® POD disposable depth filter system. It is ideal for a wide variety of primary and secondary clarification applications, including cell cultures.

Millistak+® Pod filters are available in three distinct series of media grades in order to meet specific application needs. Millistak+® DE, CE and HC media deliver optimal performance through gradient density matrix as well as positive surface charge properties.

The virus can also, if desired, be formulated into the final buffer in this step.

Thus, in one embodiment in the filtration step, concentrated and conditioned adenovirus material is provided in a final or near final formulation.

In one embodiment the process comprises two or more filtration steps.

In one embodiment the downstream processing comprises Millistak+POD system 35 CE and 50 CE cassettes followed by an opticap XL 10 express 0.5/0.2 um membrane filter in series.

Ion exchange (IEX) chromatography binds DNA very strongly and typically is the place where any residual DNA is removed. The ion exchange resin/membrane binds both the virus and the DNA and during salt gradient elusion the virus normally elutes off the column first (low salt gradient) and the DNA is eluted at a much higher salt concentration since the interaction of the DNA with the resin is stronger than the virus.

In one embodiment the chromatography step or steps employ monolith technology, for example available from BIA Separations. Monolithic columns contain highly cross-linked porous polymethacrylate material with well-defined channel size distribution.

In one embodiment the chromatography is ion-exchange, for example two stage ion-exchange. Exchanges are available from, for example GE Health BioSciences AB, cytiva and Sartorius.

Strong ion-exchanges (such as Q, S and SP) perform over a broad pH range. Q binds "proteins" with an isoelectric point under pH 7.

The capacity of weak ion-exchanges (such as DEAE, ANX and CM) to exchange varies with pH Sartobind Q are strong ion exchanges suitable for the purification of adenoviruses.

Source 15Q (from cytiva) is a polymeric, strong anion exchanger designed for polishing steps, suitable for use in industrial applications.

In one embodiment at least two chromatography steps are performed, for example wherein at least one is ion-exchange.

In one embodiment at least two ion-exchange steps are performed.

In one embodiment at least two chromatographic steps include one ion-exchange step and one liquid chromatography step.

In one embodiment after purification the virus prepared contains less than 80 ng/mL of contaminating DNA, for example between 60 ng/mL and 10 ng/mL.

In one embodiment substantially all the contaminating DNA fragments are 700 base pairs or less, for example 500 bp or less, such as 200 bp or less.

In one embodiment residual benzonase content in the purified virus product is 1 ng/mL or less, such as 0.5 ng/mL or less.

In one embodiment the residual host cell protein content in the purified virus product in 20 ng/mL or less, for example 15 ng/mL or less, in particular when measured by an ELISA assay.

In one embodiment residual tween in the purified virus product is 0.1 mg/mL or less, such as 0.05 mg/mL or less.

In one embodiment there is provided isolated purified group B adenovirus according to the present disclosure wherein the contaminating DNA content is less than 80 ng/mL.

In one embodiment the virus of the disclosure, such as an oncolytic virus of the present disclosure comprises one or more transgenes, for example one or more transgenes encoding therapeutic peptide(s) or protein sequence(s).

In one embodiment the virus encodes a therapeutic polynucleotide, for example a therapeutic RNA molecule.

In one embodiment a virus such as an oncolytic virus encodes at least one transgene. Suitable transgenes include so called suicide genes such as p53; polynucleotide sequences encoding cytokines such as IL-2, IL-6, IL-7, IL-12, IL-15, IL-18, IL-21, GM-CSF or G-CSF, an interferon (eg interferon I such as IFN-alpha or beta, interfon II such as IFN-gamma), a TNF (eg TNF-alpha or TNF-beta), TGF-beta, CD22, CD27, CD30, CD40, CD120; a polynucleotide encoding a monoclonal antibody, for example trastuzamab, cetuximab, panitumumab, pertuzumab, epratuzumab, an anti-EGF antibody, an anti-VEGF antibody and anti-PDGF antibody, an anti-FGF antibody.

A range of different types of transgenes, and combinations thereof, are envisaged that encode molecules that themselves act to modulate tumour or immune responses and act therapeutically, or are agents that directly or indirectly inhibit, activate or enhance the activity of such molecules. Such molecules include protein ligands or active binding fragments of ligands, antibodies (full length or fragments, such as Fv, ScFv, Fab, F(ab)'2 or smaller specific binding fragments), or other target-specific binding proteins or peptides (e.g. as may be selected by techniques such as phage display etc), natural or synthetic binding receptors, ligands or fragments, specific molecules regulating the transcription or translation of genes encoding the targets (e.g. siRNA or shRNA molecules, transcription factors). Molecules may be in the form of fusion proteins with other peptide sequences to enhance their activity, stability, specificity etc (e.g. ligands may be fused with immunoglobulin Fc regions to form dimers and enhance stability, fused to antibodies or antibody fragments having specificity to antigen presenting cells such as dendritic cells (e.g. anti-DEC-205, anti-mannose receptor, anti-dectin). Transgenes may also encode reporter genes that can be used, for example, for detection of cells infected with the "insert-bearing adenovirus", imaging of tumours or draining lymphatics and lymph nodes etc.

In one embodiment the cancer cell infected with an oncolytic virus is lysed releasing the contents of the cell which may include the protein encoded by a transgene.

In one embodiment the process is a GMP manufacturing process, such as a cGMP manufacturing process. In one embodiment the process further comprises the step formulating the virus in a buffer suitable for storage. In one embodiment the present disclosure extends to virus or viral formulations obtained or obtainable from the present method.

Known methods for cell lysis include employing lysis buffer, for example comprising 1% Tween-20Freeze-thawing multiple times is also a routine method of cell lysis. Pulmozyme may also be employed in cell lysis. Alternative methods for cell lysis include centrifuging cell suspension at 1000×g, 10 min at 4° C. Resuspending the cell pellet into 1 ml of Ex-Cell medium 5% glycerol and releasing the viruses from the cells by freeze-thaw by freezing tubes containing the responded cells from the pellet in liquid nitrogen for 3-5 minutes and thaw at +37° C. water bath until thawed. Generally, the freeze and thaw step is repeated twice more. This cycle releases viruses from the cells. After the last thaw step the cell debris is removed by centrifugation, for example for 1936×g, 20 min at +4° C., and host cell DNA is removed by digesting with benzonase.

In the context of the present application, medium and media may be used interchangeably. In the context of this specification "comprising" is to be interpreted as "including".

Aspects of the invention comprising certain elements are also intended to extend to alternative embodiments "consisting" or "consisting essentially" of the relevant elements. Where technically appropriate, embodiments of the invention may be combined.

Technical references such as patents and applications are incorporated herein by reference.

Any embodiments specifically and explicitly recited herein may form the basis of a disclaimer either alone or in combination with one or more further embodiments.

The present application claims priority from GB 1909081.0, filed 25 Jun. 2019 and incorporated herein by reference. The priority application may be employed as the basis for correction to the present specification.

The present invention is further described by way of illustration only in the following examples.

EXAMPLES

Example 1—Assessing Standard Purification Process for Purification of Group B Adenoviruses FIG. 2A shows a standard known purification process for adenovirus vectors. An EnAd virus was subjected to this standard purification process.

| Ad11/3 Vector | Vector #1 | Vector #1 | Vector #1 | Vector #2 |
|---|---|---|---|---|
| Drug Substance (ng HCP/2 × $10^{12}$ vp) | 11,692 | 7,869 | 2,991 | 1,298 |

A significant quantity of host cell protein remains in the final product even after purification using the standard process.

Example 2—Modified Purification Process for Group B Adenoviruses

Figure 3:
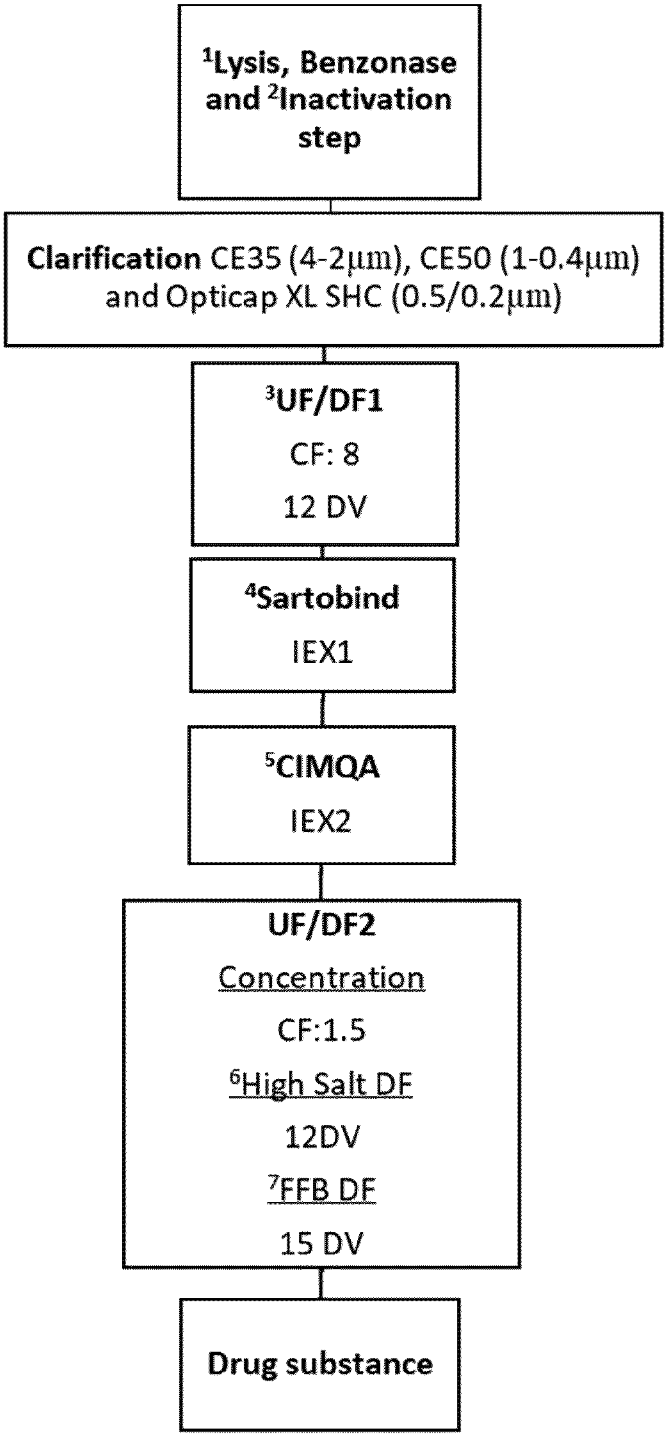

FIG. 2B shows a modified purification process of the present disclosure on an EnAd encoding a transgene between the L5 and the E4 region. After step-4 of the known process new step 5 was added. New step 5 is a diafiltration step using a diafiltration-buffer with a high salt content. FIG. 3 sets out the technical details of the process in FIG. 2B.

Step 1 HEK293 infected with the virus were lysed using the lysis-buffer:

- Benzonase (low salt buffers are required during benzonase treatment because high concentrations of salt inactivate the enzyme);
- The benzonase was then inactivated employing using an inactivation-buffer: 4.3M NaCl, 0.05M HEPES at pH 7.5;

Step 2 Clarification was performed using two depth filers. Filter 1 was pod depth filter CE35 (4 to 2 μm), from Merck Millipore, followed by filtration through pod depth filter CE50 (1-0.4 μm) also from Merck Millipore. The final stage in the clarification was to filter the composition using Opticap® XL disposable capsule filters with Millipore Express® SHC 0.5/0.2 μM hydrophilic membrane;

Step 3 Tangential follow ultrafiltration/diafiltration (UF/DF) in a Biomax V screen cassette employing a concentration factor (CF) of 8, 12 diavolumes (DV) and a diafiltration-buffer of 1M NaCl, 0.05M HEPES, 1.0% m/V Tween 20, 1.0% glycerol at pH 7.5;

Step 4 The composition obtained from step 3 was subjected to ion-exchange chromatography with a Sartobind® IEX1 system using an elution buffer: 0.45M NaCl, 0.05M HEPES, 1.0% m/V Tween 20 at pH 7.5 (step 4*a*), followed ion-exchange chromatography with a CIMQA IEX2 system using an elution buffer: 0.4M NaCl, 0.05M Tris, 0.002M $MgCl_2$, 5% glycerol at pH 7.8 (step 4*b*);

Step 5 The composition from step 4, was filtered using tangential flow ultrafiltered/diafiltered in a hollow fibre cartridge with a concentration of 1.5, employ 12 diavolumes of a diafiltration-buffer with a high salt concentration: 3M NaCl, 0.05M HEPES,k 1.0% m/V Tween 20, 1.0% m/V glycerol at pH 7.5 (step 5*a*); and

- Buffer exchange employing 15 diavolumes of a final formulation buffer (FFB) of 0.005M HEPES, 20% m/V glycerol at pH 7.8 (step 5*b*), At the end of the modified purification process, the adenoviruses and host cell proteins were again quantified using the method described above in Example 1. The host proteins were below the limit of quantification after purification. Thus, as a result of the inclusion of the additional diafiltration process, the amount of contaminating host cell protein in the final product was dramatically reduced to below the level of quantification.

Table 2 shows the viral particle obtained and the host cell protein content at various points in the purification process with an additional diafiltration step

| Process Stage | vp/ml | Total vp | % Recovery | HCP (ng/2E12 vp) |
|---|---|---|---|---|
| Post Step 2 | 1.52E+11 | 1.15E+16 | na | 5.75E+05 |
| Post Step 3 | 3.81E+11 | 4.90E+15 | 43 | 714 |
| Post Step 4a | 2.36E+12 | 3.34E+15 | 29 | 158 |
| Post Step 4b | 2.91E+12 | 2.92E+15 | 27 | 104 |
| Post Step 5a | 2.82E+12 | 2.99E+15 | 26 | Below LOQ |
| Final Formulation | 2.69E+12 | 2.95E+15 | 26 | Below LOQ |

Example 3—Single Step Purification Process for Group B Adenoviruses

Figure 4:
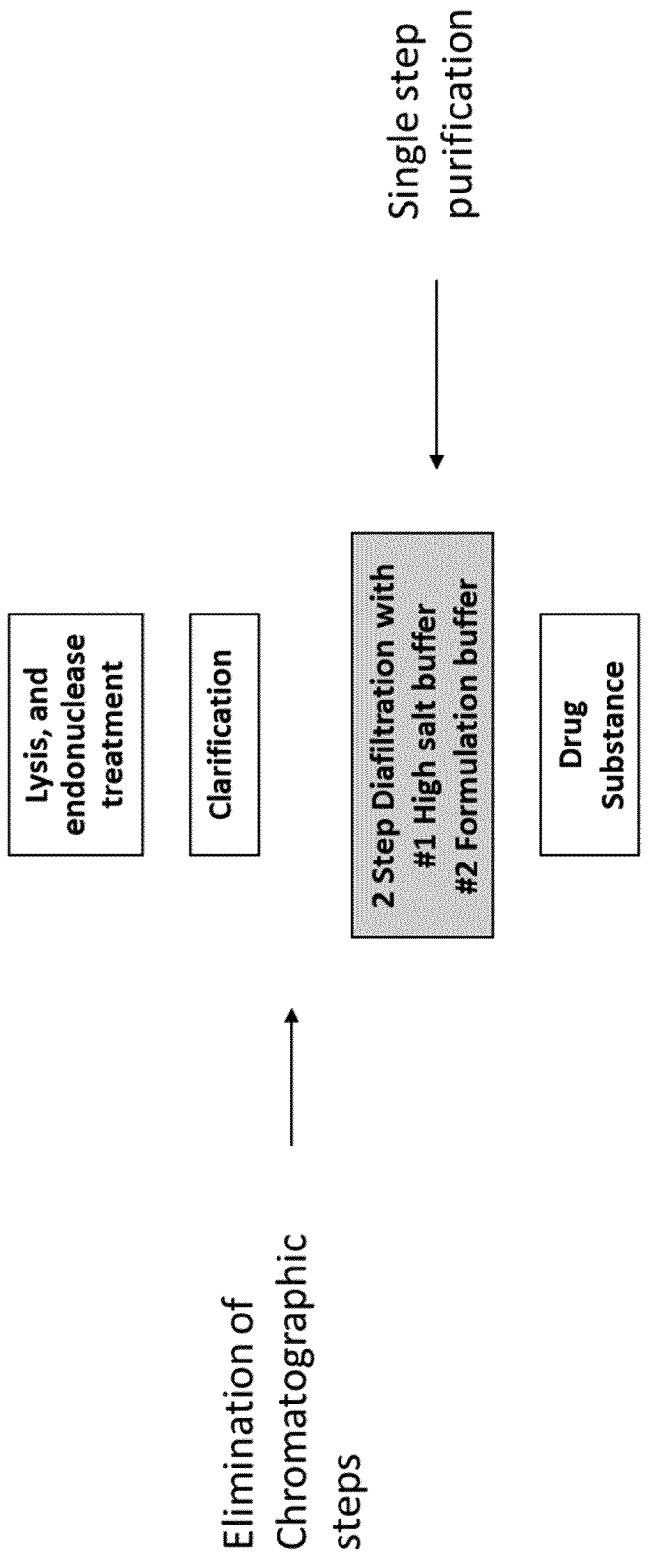
Figure 5:
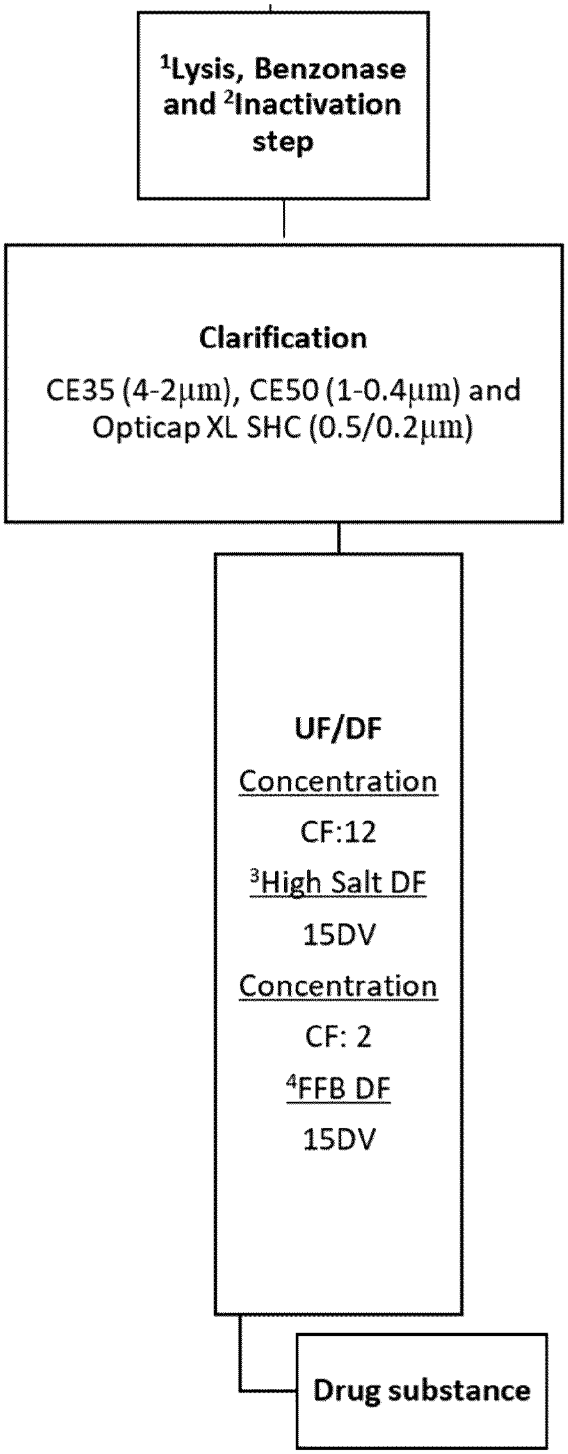
FIG. 5 shows the technical details of the single-step purification process depicted in FIG. 4.

The possibility of completely omitting the chromatography steps was investigated. FIG. 4 shows the design of a purification process which, after step 1 and 2 (lysis, endonuclease treatment, inactivation and clarification), only has a defiltration step. The technical details for this process are shown in FIG. 5. The process was performed with an EnAd virus encoding a transgene.

Step 1, and 2 are as detailed above in Example 2. Step 2 is then followed by a diafiltration as described above in step 5. The results are shown below in Table 2.

TABLE 3

| Process Stage | vp/ml | Total vp | % Recovery | HCP (ng/ml) | HCP (ng/2E12 vp) |
|---|---|---|---|---|---|
| Post Step 2 | 6.39E+10 | 3.26E+14 | na | 2.31E+04 | 7.23E+05 |
| Final Formulation | 4.69E+11 | 9.85E+13 | 30 | Below LOQ | na |

As can be seen, the levels of host cell protein employing just the diafiltration step was below the level of quantification. Thus, a similar level of purity was achieved using the single step purification compared to the modified purification process containing three different purification steps. Hence, this provides good evidence that the chromatography step can be either omitted or performed together with the diafiltration step in order to produce a final group B adenovirus product of high purity.

The invention claimed is:

1. A method for purifying a replication competent group B adenovirus from host cell proteins, comprising a purification step of:

- subjecting a composition comprising said group B adenovirus to diafiltration employing a diafiltration-buffer with a high salt concentration, wherein said salt concentration is in the range of 2.5 M to 5.5 M.

2. The method according to claim 1, wherein the diafiltration-buffer has a conductivity of at least 180 mScm−1.

3. The method according to claim 1, wherein the buffer comprises a salt selected from a chloride salt, a sulfate salt, any salt fully soluble and dissociated in water, and combinations thereof.

4. The method according to claim 1, wherein the diafiltration-buffer comprises one or more of the following: an alkaline earth metal salt, sodium acetate, Tris, Bis-Tris, $NaH_2PO_4$, NaCl, and KCl.

5. The method according to claim 1, wherein the diafiltration-buffer is selected from: meglumine buffer, Gly-NaCl buffer, and TRIS buffer.

6. The method according to claim 5, wherein the diafiltration-buffer comprises HEPES.

7. The method according to claim 1, wherein the diafiltration-buffer is at a pH in the range 7 to 9.8.

8. The method according to claim 1, wherein the diafiltration employs an ultrafiltration membrane at least 300 KDa or greater.

9. The method according to claim 1, wherein the diafiltration has a flow rate of 1 to 3 $m^2/s$.

10. The method according to claim 1, wherein the diafiltration is carried out employing a hollow fiber cartridge or flat membrane cassette filter.

11. The method according to claim 10, wherein the diafiltration is performed using a tangential flow filtration (TFF), and wherein the TFF is performed using a consistent volume method.

12. The method according to claim 1, wherein the diafiltration is performed using at least 8 diavolumes of high salt diafiltration-buffer.

13. The method according to claim 1, wherein the diafiltration comprises two steps.

14. The method according to claim 13, wherein a first step of the diafiltration is diafiltration with the high salt diafiltration-buffer.

15. The method according to claim 13, wherein a second step of the diafiltration is diafiltration with a final formulation buffer.

16. The method according to claim 1, wherein only one diafiltration-buffer is employed.

17. The method according to claim 1, comprising a further purification step comprising subjecting the composition to a chromatography purification.

18. The method according to claim 17, wherein the chromatography purification employs ion-exchange chromatography.

19. The method according to claim 1, wherein the method does not employ chromatography.

20. The method according to claim 1, wherein the composition comprising the group B adenovirus is a clarified cell lysate obtained by:

lysing host cells comprising the group B adenovirus to obtain a crude cell lysate;

contacting the crude cell lysate with an endonuclease to obtain an endonuclease-treated cell lysate; and subjecting the endonuclease-treated cell lysate to filtration to obtain the clarified cell lysate.

21. The method according to claim 20 wherein a second filter is employed in the step of subjecting the endonuclease-treated cell lysate to filtration to obtain the clarified cell lysate.

22. The method according to claim 1, which comprises a filtration step comprising passing the composition through a 0.2 μm filter.

23. The method according to claim 1, wherein the group B adenovirus comprises a sequence of formula (I):

$$5'ITR\text{-}B_1\text{-}B_A\text{-}B_2\text{-}B_X\text{-}B_B\text{-}B_Y\text{-}B_3\text{-}3'ITR \quad \text{(I)}$$

wherein:

$B_1$ is bond or comprises: E1A, E1B or E1A-E1B;

$B_A$ comprises: E2B-L1-L2-L3-E2A-L4;

$B_2$ is a bond or comprises: E3;

$B_X$ is a bond or a DNA sequence comprising: a restriction site, one or more transgenes or both;

$B_B$ comprises L5;

$B_Y$ is a bond or a DNA sequence comprising: a restriction site, one or more transgenes or both; and $B_3$ is a bond or comprises: E4, wherein at least one of $B_X$ or $B_Y$ is not a bond.

* * * * *